United States Patent
Henkel et al.

(10) Patent No.: US 9,522,065 B2
(45) Date of Patent: *Dec. 20, 2016

(54) AUTOMATED IMPLANTABLE PENILE PROSTHESIS PUMP SYSTEM

(71) Applicant: AMS Research, LLC, Minnetonka, MN (US)

(72) Inventors: Gregory J. Henkel, Chanhassen, MN (US); Gary A. Rocheleau, Maple Grove, MN (US); Scott E. Jahns, Hudson, WI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,567

(22) Filed: Jul. 22, 2015

(65) Prior Publication Data

US 2016/0015519 A1    Jan. 21, 2016

Related U.S. Application Data

(63) Continuation of application No. 13/804,000, filed on Mar. 14, 2013, now Pat. No. 9,089,426.

(60) Provisional application No. 61/613,770, filed on Mar. 21, 2012.

(51) Int. Cl.
*A61F 5/00* (2006.01)
*A61F 2/26* (2006.01)

(52) U.S. Cl.
CPC ..................................... *A61F 2/26* (2013.01)

(58) Field of Classification Search
CPC ......... A61F 5/41; A61F 2/26; A61F 2005/415

USPC ....................................................... 600/38–41
See application file for complete search history.

(56) References Cited

U.S. PATENT DOCUMENTS

| | | |
|---|---|---|
| 525,020 A | 8/1894 | Jungner |
| 734,498 A | 7/1903 | Bachlet |
| 2,455,859 A | 12/1948 | Foley |
| 2,533,924 A | 12/1950 | Foley |
| 3,538,917 A | 11/1970 | Selker |
| 3,642,005 A | 2/1972 | McGinnis |
| 3,720,200 A | 3/1973 | Laird |

(Continued)

FOREIGN PATENT DOCUMENTS

| | | |
|---|---|---|
| EP | 0065853 | 1/1982 |
| EP | 0051420 | 12/1982 |

(Continued)

OTHER PUBLICATIONS

Ferguson, Cespedes, "Prospective Long-term results and quality-of-life assessment after Dura-II penile prosthesis placement," Urology 61: 437-441, 2003.

(Continued)

*Primary Examiner* — John Lacyk
(74) *Attorney, Agent, or Firm* — Brake Hughes Bellermann LLP

(57) ABSTRACT

A dual poppet valve assembly for a pump assembly of an implantable penile prosthesis having a suction poppet engagable by a plurality of fingers allowing free travel of the poppet and to prevent vacuum lockup of the pump assembly. The suction poppet can also include an elongated shaft receivable within a corresponding bore of a cylinder poppet to prevent the suction poppet from becoming misaligned during the operation of the pump assembly.

15 Claims, 4 Drawing Sheets

(56) References Cited

U.S. PATENT DOCUMENTS

| | | |
|---|---|---|
| 3,744,063 A | 7/1973 | McWhorter |
| 3,750,194 A | 8/1973 | Summers |
| 3,853,122 A | 12/1974 | Strauch |
| 3,863,622 A | 2/1975 | Buuck |
| 4,222,377 A | 9/1980 | Burton |
| 4,224,370 A | 9/1980 | Heinemann |
| RE31,121 E | 1/1983 | Teinicke |
| 4,386,601 A | 6/1983 | Trick |
| 4,408,597 A | 10/1983 | Tenney, Jr. |
| 4,412,530 A | 11/1983 | Burton |
| 4,417,567 A | 11/1983 | Trick |
| 4,419,985 A | 12/1983 | Trick |
| 4,502,159 A | 3/1985 | Woodroof |
| 4,549,531 A | 10/1985 | Trick |
| 4,550,720 A | 11/1985 | Trick |
| 4,553,533 A | 11/1985 | Leighton |
| 4,566,446 A | 1/1986 | Fogarty |
| 4,584,990 A | 4/1986 | Haber |
| 4,634,443 A | 1/1987 | Haber |
| 4,682,583 A | 7/1987 | Burton |
| 4,708,140 A | 11/1987 | Baron |
| 4,829,990 A | 5/1989 | Thuroff |
| 4,834,115 A | 5/1989 | Stewart |
| 4,878,889 A | 11/1989 | Polyak |
| 4,969,474 A | 11/1990 | Schwarz |
| 4,994,020 A | 2/1991 | Polyak |
| 5,012,822 A | 5/1991 | Schwarz |
| 5,078,676 A | 1/1992 | Bailly |
| 5,088,980 A | 2/1992 | Leighton |
| 5,097,848 A | 3/1992 | Schwarz |
| 5,141,509 A | 8/1992 | Burton et al. |
| 5,370,690 A | 12/1994 | Barrett |
| 5,562,598 A | 10/1996 | Whalen |
| 5,570,690 A | 11/1996 | Yoon |
| 5,634,878 A | 6/1997 | Grundei |
| 5,782,916 A | 7/1998 | Pintauro |
| 5,851,176 A | 12/1998 | Willard |
| 5,893,826 A | 4/1999 | Salama |
| 5,989,288 A | 11/1999 | Pintauro |
| 6,013,102 A | 1/2000 | Pintauro |
| 6,063,119 A | 5/2000 | Pintauro |
| 6,095,969 A | 8/2000 | Karram |
| 6,171,233 B1 | 1/2001 | Willard |
| 6,183,520 B1 | 2/2001 | Pinaturo |
| 6,328,687 B1 | 12/2001 | Karram |
| 6,354,991 B1 | 3/2002 | Gross |
| 6,432,038 B1 | 8/2002 | Bakane |
| 6,432,040 B1 | 8/2002 | Meah |
| 6,443,887 B1 | 9/2002 | Derus |
| 6,464,999 B1 | 10/2002 | Huo |
| 6,533,719 B2 | 3/2003 | Kuyava |
| 6,652,449 B1 | 11/2003 | Gross |
| 6,659,937 B2 | 12/2003 | Polsky |
| 6,689,046 B2 | 2/2004 | Sayet |
| 6,712,772 B2 | 3/2004 | Cohen |
| 6,723,042 B2 | 4/2004 | Almli |
| 6,730,017 B2 | 5/2004 | Henkel |
| 6,749,556 B2 | 6/2004 | Banik |
| 6,862,480 B2 | 3/2005 | Cohen |
| 6,896,651 B2 | 5/2005 | Gross |
| 6,915,165 B2 | 7/2005 | Forsell |
| 6,921,360 B2 | 7/2005 | Banik |
| 6,935,847 B2 | 8/2005 | Kuyava |
| 6,991,601 B2 | 1/2006 | Kuyava |
| 7,128,707 B2 | 10/2006 | Banik |
| 7,169,103 B2 | 1/2007 | Ling |
| 7,244,227 B2 | 7/2007 | Mornngstar |
| 7,250,026 B2 | 7/2007 | Kuyava |
| 7,350,538 B2 | 4/2008 | Kuyava |
| 7,387,603 B2 | 6/2008 | Gross |
| 7,400,926 B2 | 7/2008 | Forsell |
| 7,407,482 B2 | 8/2008 | Kuyava |
| 7,874,978 B2 | 1/2011 | Kuyava et al. |
| 9,089,426 B2 * | 7/2015 | Henkel ................ A61F 2/26 |
| 2004/0167574 A1 | 8/2004 | Kuyava |
| 2005/0075534 A1 | 4/2005 | Kuyava |
| 2008/0114202 A1 | 5/2008 | Kuyava et al. |
| 2009/0132043 A1 | 5/2009 | George |

FOREIGN PATENT DOCUMENTS

| | | |
|---|---|---|
| EP | 0137752 | 4/1985 |
| EP | 00682923 | 11/1995 |
| GB | 2160777 | 1/1986 |
| GB | 2192546 | 1/1988 |
| WO | WO80/00302 | 3/1980 |
| WO | WO85/00513 | 2/1985 |
| WO | WO86/01398 | 3/1986 |
| WO | WO94/04095 | 3/1994 |
| WO | WO96/04865 | 2/1996 |
| WO | WO02/051339 | 7/2002 |
| WO | WO2005/032428 | 4/2005 |
| WO | WO2005/034815 | 4/2005 |
| WO | WO2006/066199 | 6/2006 |

OTHER PUBLICATIONS

Henry, Gerald, "Advances in penile prosthesis design," Current Sexual Health Reports, 2007, 4:15-19.

Kardar et. al., "An unusual complication of penile prosthesis following urethroplasty," Scand J. Urol. Nephrol 36:89-90, 2002.

Kaufman and Raz, "Use of implantable prostheses for the treatment of urinary incontinence and impotence," Am. J. Surg. Aug. 1975 US30 (2) p. 244-250.

Khoudary, et al., "Design considerations in penile prosthesis: the american medical system product line," J. Long-term effects of Medical Implants, 7(1): 55-64 (1997).

Lazarou et. al., "Technical advances in penile prosthses," J. Long-term effects of Medical Implants, 16(3): 235-247 (2006).

Merino, "Penile prosthesis for the treatment of erectile dysfunciton," Actas Ural Esp 2006; 30 (2): 159-169.

Montague and Angermeier, "Current status of penile prosthesis implantation," Current Urology Reports 2000, 1:291-296.

Montague and Angermeier, "Contemporary aspects of penile prosthesis implantation," Urol Int. 2003;70:141-146.

Montague and Angermeier, "Surgical approaches for penile prosthesis implantation: penoscrotal vs infrapubic," Int. J. Impotence Research (2003) 15, Supp 5, S134-S135.

Montague, "Penile prosthesis implantation for end-stage erectile dysfunction after radial prostatectomy ," MedReviews, Inc. 2005, pp. S51-S57.

Montague et. al., "Clinical guidelines panel on erectile dysfunciton: summary report on the treatment of organic erectile dysfunction," J. Urology, vol. 156, 2007-2011, Dec. 1996.

Mulcahy, "Another look at the role of penile prostheses in the management of impotence," Urology Annual 11, pp. 169-185 (1997).

Randrup, "Penile implant surgery: rear tip extender that stays behind," Urology, Jan. 1992, vol. XXXIX, No. 1., 1 pg.

Minervini, "Outcome of penile prosthesis implantation for treating erectile dysfunction: experience with 504 procedures," BJU Int. 97, pp. 129-133 (2005).

* cited by examiner

AUTOMATED IMPLANTABLE PENILE PROSTHESIS PUMP SYSTEM

RELATED APPLICATION

The present-application is a continuation application of U.S. Ser. No. 13/804,000, filed Mar. 14, 2013, which claims the benefit of U.S. Provisional Application No. 61/613,770, filed Mar. 21, 2012, and entitled "AUTOMATED IMPLANTABLE PENILE PROSTHESIS PUMP SYSTEM", which are incorporated herein by reference in their entireties.

FIELD OF THE INVENTION

The present invention is generally directed to a pump system for an implantable penile prosthesis. Specifically, the present invention is directed to a suction poppet assembly for an implantable penile prosthesis pump system.

BACKGROUND OF THE INVENTION

Implantation of an implantable penile prosthesis (IPP) is a common surgical procedure for treating erectile dysfunction and other penile ailments. An IPP comprises an inflatable cylinder connected by a pump to a separate reservoir for holding the quantity of fill liquid via kink resistant tubing. This version of the IPP is available under the trade name AMBICOR from American Medical Systems of Minnetonka, Minn. Typically, the entire IPP is implanted into the patient's body with the inflatable cylinder being placed in the corpus cavernosum and the pump being placed within the scrotum. The reservoir can also be placed within the scrotum or placed elsewhere within the pelvic region. To operate the IPP, the pump is manually actuated to transfer fill liquid from the integrated or implanted reservoir into the inflatable cylinder to fill and pressurize the inflatable cylinder.

A typical pump system for an IPP comprises a pump bulb that can be compressed to draw fluid from a reservoir and push the inflation fluid into the inflatable cylinder. Generally, the pump is compressed and released to draw fluid from the reservoir into the pump. The pump is compressed again to force fluid from the pump into the inflatable cylinder. Two selective poppet valves are positioned along the flow path between reservoir and inflatable cylinder to control the direction of the fluid flow through the pump system.

Typically, the IPP and the pump system are provided to the medical personnel without any working fluid within the system. Prior to implantation, each component of the IPP is filled or nearly filed with the working fluid by the medical personnel. The medical personnel also often test the operation of the IPP to insure that the all the components of the IPP are functioning properly prior to implantation. However, if too much air remains in the IPP when the pump system is operated by the medical personnel or the patient, the air within the system can cause pump to lock up. Specifically, the pump bulb can remain compressed after being actuated rather than re-expanding to draw additional fluid into the pump bulb.

Another drawback of the pump system is that the poppet valves can become misaligned during filling and operation of the IPP and pump system. If the poppet becomes misaligned, uncontrolled leakage can occur allowing fluid to travel through the fluid pathway. Similarly, the misaligned poppet can become stuck preventing any operation of the poppet.

As such, there is a need for a pump system for an IPP that can be operated by medical personnel with a reduced risk of damage or malfunction during test operation.

SUMMARY OF THE INVENTION

The present invention is directed to an IPP having a valve assembly comprising a dual poppet design. The valve assembly is integrated into a pump assembly comprising a pump bulb that can be actuated to transfer working fluid from a reservoir to at least one inflatable cylinder. The valve assembly defines a valve flow path, for example, a generally linear flow path, between the reservoir and the inflatable cylinder. The valve flow path intersects the opening to the pump bulb such that actuating the pump bulb moves fluid along the flow path. In one aspect, the valve flow path also defines a suction annulus positioned in the valve flow path between the reservoir and the pump bulb. Similarly, the valve flow path can also define a cylinder annulus positioned between the pump bulb and the cylinder.

In one aspect, the valve assembly comprises a suction poppet engagable to the suction annulus and a cylinder poppet engagable to the cylinder annulus. Each poppet is movable along a central axis defined by the flow path between an engaged position in which the poppet is engaged to its corresponding annulus to prevent the flow of working fluid through the annulus and a disengaged positioned wherein the poppet is positioned to allow working fluid to pass through the corresponding annulus. In one aspect, the poppets are both biased to the engaged position to prevent flow of working fluid until the pump bulb is actuated. The suction poppet is positioned on the pump bulb side of the suction annulus such that releasing the compressed pump bulb creates a suction that pulls the suction poppet into the disengaged position and draws a quantity of working fluid through the suction annulus into the pump bulb. In contrast, the cylinder poppet is positioned on the opposite side of the cylinder annulus from the pump bulb, wherein compressing the pump bulb creates a positive pressure pushing the cylinder poppet into the disengaged position and a forcing a quantity of working fluid through the cylinder annulus into the inflatable cylinder.

In one aspect, the flow path further defines an annular ring positioned between the suction annulus and the pump bulb opening. If the pump bulb is actuated too quickly and/or air is present within the pump bulb opening such as, for example, during the initial installation, the suction poppet can become wedged against the annular ring blocking all flow and creating a vacuum condition essentially locking the pump bulb in the compressed state. In one aspect, the suction poppet can further comprise a head extending through the suction annulus. The head can define a lip engagable by a plurality of fingers extending from the suction annulus. The fingers engage the lip when the suction poppet is slid into the disengaged position to prevent the suction poppet from engaging the annular ring and creating vacuum lock up. The fingers allow for a controlled travel distance of the suction poppet preventing vacuum lock up of the pump bulb.

In one aspect, the suction puppet can further comprise an elongated suction poppet shaft extending through the cylinder annulus. In this configuration, a cylinder poppet can define defines a cylinder poppet bore for slidably receiving the elongated suction poppet shaft. If the suction poppet becomes misaligned, the suction poppet may not properly engage the suction annulus allowing working fluid to leak through the suction annulus. The cylinder poppet bore guides the suction poppet to maintain an axial alignment of the suction poppet along a valve chamber axis as the suction poppet moves between the engaged position and the disengaged position relative to suction annulus.

In one aspect, the valve assembly can further comprise a release button that can be pressed against an elongated head of the suction poppet to push the suction poppet to the disengaged position along the valve chamber axis without operating the pump bulb. The elongated suction poppet shaft can be used to push against an end of the cylinder poppet bore such that both the suction poppet and the cylinder poppet are positioned in the disengaged position allowing free flow through the valve flow path. The release button can be used to return the working fluid to the reservoir from the inflatable cylinder. The release button can also be used to reset the operation of the valve assembly.

A method of preventing vacuum lock up of the pump bulb, according to an aspect of the present invention, can comprise providing a suction poppet positioned between the suction annulus leading to the reservoir and the pump bulb, wherein the suction poppet further comprises an elongated head extending through the suction annulus. The method can further comprise defining a plurality of fingers extending from the suction annulus to limit the travel distance of the suction poppet and prevent uncontrolled engagement of the suction poppet to other features within the valve assembly.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

Figure 1:
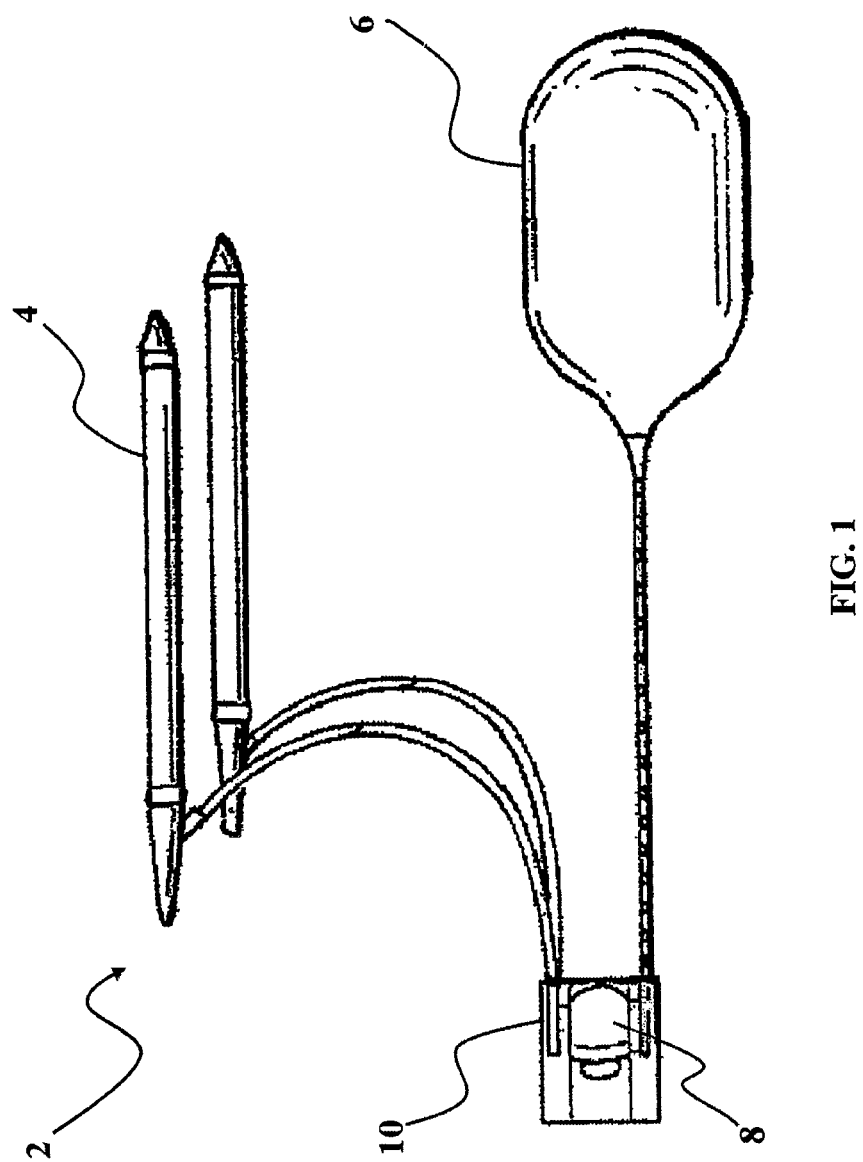
FIG. 1 is a top view of a implantable penile prosthesis according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

As shown in FIG. 1, an implantable penile prosthesis (IPP) 2, according to an embodiment of the present invention, comprises at least one inflatable cylinder 4, a reservoir 6, a pump 8 and a valve assembly 10. The pump 8 can further comprise a pump bulb 12 that can be compressed and released to draw and pump working fluid. The IPP 2 generally operates by actuating the pump bulb 12 to draw a quantity of working fluid from the reservoir 6 and pumping the working fluid into the inflatable cylinder 4. The valve assembly 10 is generally adapted to prevent back flow of the working fluid during operation of the pump 8 to inflate inflatable cylinder 4.

Figure 2:
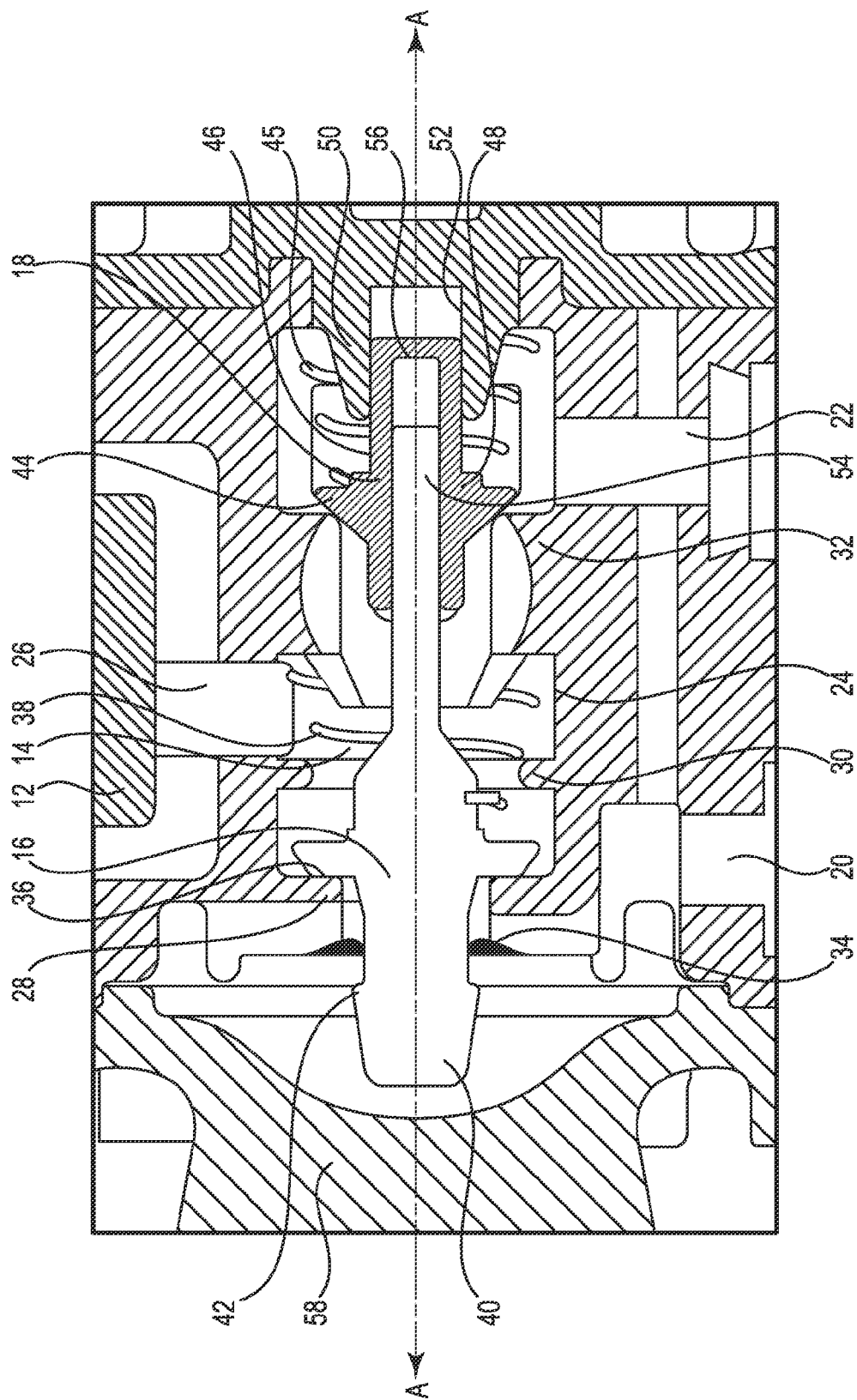
FIG. 2 is a partial cross-sectional view of a valve assembly according to an embodiment of the present invention.
Figure 4:
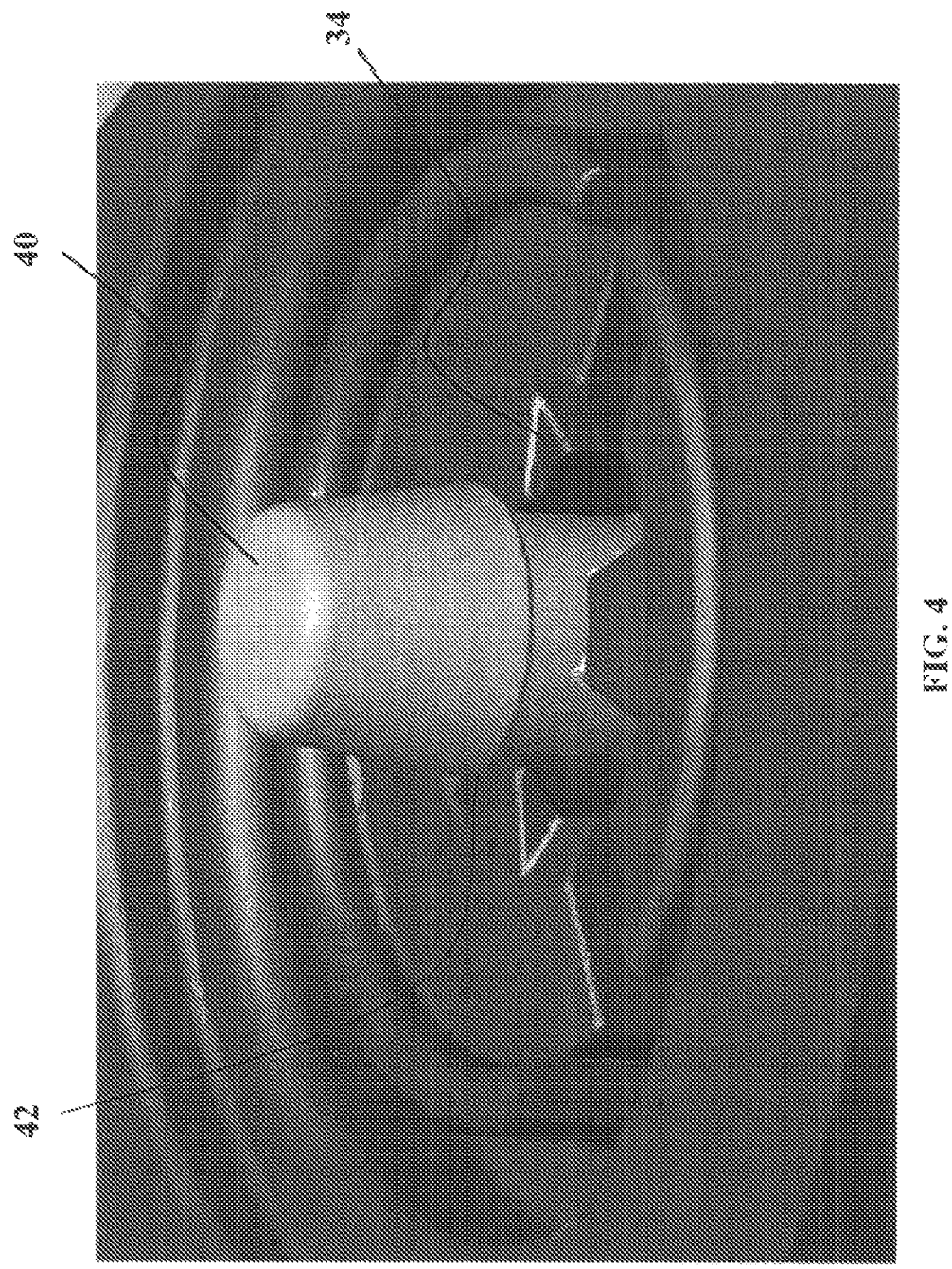
FIG. 4 is a perspective view of a suction annulus with a head of the suction poppet extending through annulus according to an embodiment of the present invention.

As shown in FIGS. 1-2, the valve assembly 10 defines a valve flow path 14 and comprises a suction poppet 16 and a cylinder poppet 18. The valve flow path 14 is defined between a reservoir inlet 20 from the reservoir 6 and a cylinder outlet 22 leading to the cylinder 4. The valve flow path 14 also further comprises a linear valve chamber 24 extending along a central valve chamber axis a-a. The linear valve chamber 24 defines a pump bulb opening 26 providing fluid communication between the pump bulb 12 and the linear valve chamber 24. The linear valve chamber 24 also defines a suction annulus 28 and an annular ring 30 positioned between the reservoir inlet 20 and the pump bulb opening 26. Similarly, the linear valve chamber 24 also defines a cylinder annulus 32 positioned between the pump bulb opening 26 and the cylinder outlet 32. In one aspect, the suction annulus 28 further comprises a plurality of fingers 34 as shown in FIG. 4 that extend radially toward the central valve chamber axis a-a.

Figure 3:
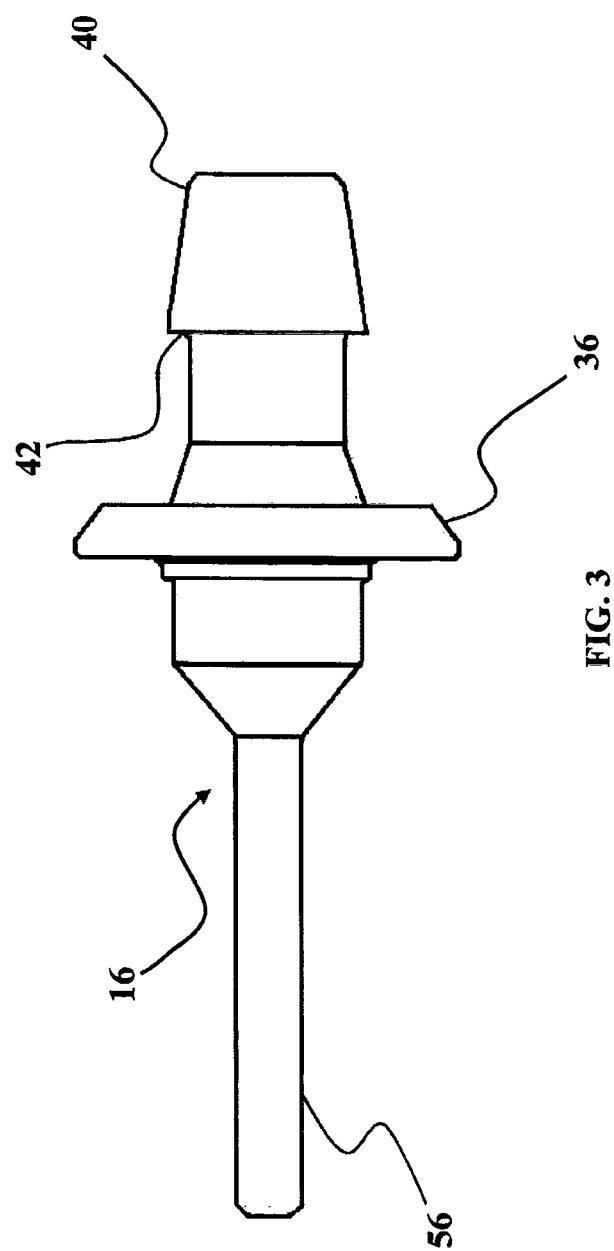
FIG. 3 is a side view of a suction poppet according to an embodiment of the present invention.

As shown in FIGS. 2-3, the suction poppet 16 defines a sealing surface 36 and is linearly movable along the central valve chamber axis a-a between an engaged position and a disengaged positioned. In the engaged position, the sealing surface 36 is engaged to the suction annulus 28 preventing flow of working fluid through the suction annulus 28. In the disengaged positioned, the sealing surface 36 is disengaged from the suction annulus 28 allowing working fluid to pass through the suction annulus 28. As shown in FIGS. 2-3, the suction poppet 16 is positioned on the pump bulb opening 26 side of the suction annulus 28 such that the suction poppet 16 is biased to maintain flow in a single direction during inflation of the cylinders 4. In one aspect, the suction poppet 16 further comprises a suction poppet spring 38 maintaining the suction poppet 16 in the engaged position to prevent flow through the valve flow path 14 without operation of the pump bulb 12.

In one aspect, the suction poppet 16 further comprises an elongated head 40 extending through the suction annulus 28 and defining a lip 42 engagable by the plurality of fingers 34 when the suction poppet 16 moves toward the disengaged position limiting the travel distance of the suction poppet 16 and preventing the suction poppet 16 from engaging the annular ring 30.

As shown in FIG. 2, the cylinder poppet 18 also defines a sealing surface 44 engagable to the cylinder annulus 32. The cylinder poppet 18 is also movable along the central valve chamber axis a-a between an engaged position in which the sealing surface 44 is engaged to the cylinder annulus 32 preventing flow of working fluid through the cylinder annulus 32 and a disengaged positioned allowing working fluid to pass through the annulus 32. As shown in FIG. 2, the cylinder poppet 18 is positioned on the cylinder outlet 22 side of the cylinder annulus 32 such that the cylinder poppet 18 is biased to maintain a flow direction from the reservoir 6 to the cylinder 4 during normal operation. In one aspect, the cylinder poppet 18 further comprises a cylinder poppet spring 45 to maintain the suction poppet 16 in the engaged position to prevent flow through the valve flow path 14 without operation of the pump bulb 12.

In one aspect, the cylinder poppet 18 further comprises an elongated cylinder poppet shaft 46 and defines a lip 48. In this configuration, the valve flow path 14 further defines a cylinder journal 50 defining a journal bore 52 for receiving the elongated cylinder poppet shaft 46. The journal bore 52 guides the cylinder poppet 18 along the central valve chamber axis a-a during movement of the cylinder poppet 18 between the engaged and disengaged position such that the cylinder poppet 18 is prevented from moving along an axis transverse to the central valve chamber axis a-a. The cylinder journal 50 also engages the lip 48 of the cylinder poppet 18 when the poppet 18 moves to the disengaged position to limit the travel of the cylinder poppet 18.

In one aspect, the suction poppet 16 can further comprise an elongated suction poppet shaft 54 extending through the cylinder annulus 32. In this configuration the cylinder poppet 18 further defines a cylinder poppet bore 56 for receiving the elongated suction poppet shaft 54. The cylinder poppet bore 56 guides the elongated suction poppet shaft 54 along the central valve chamber axis a-a during movement of the suction poppet 16 between the engaged and disengaged position such that the suction poppet 16 is prevented from moving along an axis transverse to the central valve chamber axis a-a. The elongated suction poppet shaft 54 can also be used to engage the end of the cylinder poppet bore 56 to push the cylinder poppet 18 into the disengaged position.

In operation, compressing the pump bulb 12 creates a positive pressure pushing working fluid and/or air within the pump bulb 12 out of the pump bulb opening 26 into the valve flow path 14. The positive pressure also pushes against the cylinder poppet 18 moving the cylinder poppet 18 into the disengaged position forcing the fluid and/or air into the inflatable cylinder 4. Releasing the compressed pump bulb 12 allows the pump bulb 12 to expand and creates a vacuum pulling the cylinder poppet 18 into the engaged position and the suction poppet 16 into the disengaged position allowing working fluid to be drawn from the reservoir 6 into the pump bulb 12. The process can be repeated to continuously draw working fluid from the reservoir 6 to inflate the inflatable cylinder 4.

In one aspect, the valve assembly 10 can further comprise a release button 58 for allowing fluid to flow in reverse through the valve flow path 14. The release button 58 can be actuated to push against the elongated head 40 to push the suction poppet 16 into the disengaged position. In this configuration, the elongated suction poppet shaft 54 is adapted to engage the end of the cylinder poppet bore 56 to push the cylinder poppet 18 into the disengaged position. With both the suction poppet 16 and the cylinder poppet 18 are in the disengaged position with respect to the their corresponding annulus, the pressure of the working fluid within the inflatable cylinder 4 pushes working fluid through the valve flow path 14 back to the reservoir 6.

As shown in FIG. 2, a method of preventing vacuum lock up of the pump bulb 12 comprises positioning the suction poppet 16 positioned between the suction annulus 28 and the pump bulb 12, wherein the suction poppet 16 further comprises an elongated head 40 extending through the suction annulus 28. The method further comprises defining a plurality of fingers 34 extending from the suction annulus 28 to limit the travel distance of the suction poppet 16 to prevent uncontrolled engagement of the suction poppet 16 to other features within the valve assembly 10.

While the invention is amenable to various modifications and alternative forms, specifics thereof have been shown by way of example in the drawings and described in detail. It is understood, however, that the intention is not to limit the invention to the particular embodiments described. On the contrary, the intention is to cover all modifications, equivalents, and alternatives falling within the spirit and scope of the invention as defined by the appended claims.

The invention claimed is:

1. A method of moving fluid within an implantable penile prosthesis, comprising the steps of:
    implanting a penile prosthesis system comprising at least one inflatable cylinder, a reservoir, a pump comprising a pump bulb, and a valve assembly, wherein the valve assembly comprises a valve flow path defined between a reservoir inlet and a cylinder outlet, the valve flow path being fluidly connected to pump bulb opening, the valve flow path extending linearly along a central axis with a suction poppet and a cylinder poppet positioned within the valve flow path and being movable along the central axis, the cylinder poppet including an extended cylinder shaft that is slidably received within a cylinder journal disposed within the valve assembly and integral to the valve flow path, wherein the interaction of the cylinder journal and the extended cylinder shaft retain axial alignment of the cylinder poppet along the central axis as the cylinder poppet transitions between an engaged position and a disengaged position, the cylinder poppet includes a cylinder poppet bore and the suction poppet includes an elongated suction poppet shaft, the elongated suction poppet shaft being slidably received within the cylinder poppet bore to retain axial alignment of the suction poppet along the central axis; and
    compressing the pump bulb to create a positive pressure to push fluid within the pump bulb into the valve flow path and to push against the cylinder poppet, wherein the positive pressure moves the cylinder poppet into a disengaged position and forces the fluid into the at least one inflatable cylinder.

2. The method of claim 1, further comprising a step of releasing the compressed pump bulb and allowing the pump bulb to expand, thereby creating a vacuum that pulls the cylinder poppet into the engaged position, pulls the suction poppet into the disengaged position, and allows fluid to be drawn from the reservoir into the pump bulb.

3. The method of claim 2, wherein the steps of compressing the pump bulb and releasing the pump bulb are sequentially repeated at least one additional time to draw fluid from the reservoir to inflate the at least one cylinder.

4. The method of claim 2, wherein the valve assembly further comprises a release button that is actuatable along the central axis for allowing fluid to flow in an opposite direction through the valve flow path.

5. The method of claim 4, further comprising the step of actuating the release button so that the release button contacts an elongated head of the suction poppet to slidably direct the suction poppet along the central axis.

6. The method of claim 5, wherein pushing the release button against the elongated head of the suction poppet further comprises pushing the suction poppet into the disengaged position and engaging the elongated suction poppet shaft with an end of the cylinder poppet bore to push the cylinder poppet into the disengaged position.

7. The method of claim 6, wherein when the suction poppet and cylinder poppet are in the disengaged position, pressure within the inflatable cylinder is sufficient to push the fluid through the valve flow path and to the reservoir.

8. The method of claim 1, further comprising the step of preventing vacuum lock up of the pump bulb by positioning the suction poppet between a suction annulus and the pump bulb, wherein the suction poppet further comprises an elongated head extending through the suction annulus.

9. The method of claim 8, further comprising a plurality of fingers extending from the suction annulus to limit a travel distance of the suction poppet.

10. A method of moving fluid within an implantable penile prosthesis between a cylinder outlet in fluid communication with at least one cylinder and a reservoir inlet in fluid communication with a reservoir along a valve flow path, comprising the steps of:
implanting the penile prosthesis comprising the at least one cylinder, the reservoir, a pump comprising a pump bulb, and a valve assembly, wherein the valve assembly comprises:
a cylinder poppet comprising a cylinder poppet bore, a cylinder poppet sealing surface, a cylinder annulus, and a cylinder poppet spring that biases the cylinder poppet toward the cylinder annulus; and
a suction poppet comprising an elongated suction poppet shaft that is slideably engaged within the cylinder poppet bore to retain axial alignment of the suction poppet and cylinder poppet along a central axis, a suction poppet sealing surface, a suction annulus, and a suction poppet spring that biases the suction poppet toward the suction annulus;
wherein the valve flow path is defined between the reservoir inlet and the cylinder outlet, the valve flow path being fluidly connected to a pump bulb opening, the valve flow path extending linearly along the central axis with the suction poppet and the cylinder poppet positioned within the valve flow path and being movable along the central axis, the cylinder poppet further including an extended cylinder shaft that is slidably received within a cylinder journal positioned within the housing and integral to the valve flow path, wherein the engagement between the cylinder journal and extended cylinder shaft retain axial alignment of the cylinder poppet along the central axis as the cylinder poppet transitions between an engaged position and a disengaged position; and
compressing the pump bulb to create a positive pressure to push fluid within the pump bulb into the valve flow path and to push against the cylinder poppet, wherein the positive pressure moves the cylinder poppet into a disengaged position and forces the fluid into the at least one cylinder.

11. The method of claim 10, further comprising the step of releasing the compressed pump bulb and allowing the pump bulb to expand, there by creating a vacuum that pulls the cylinder poppet into the engaged position, pulls the suction poppet into the disengaged position, and allows fluid to the drawn from the reservoir into the pump bulb.

12. The method of claim 11, wherein the valve assembly further comprises a release button that is actuatable along the central axis for allowing fluid to flow in an opposite direction through the valve flow path.

13. The method of claim 10, wherein the cylinder poppet spring is positioned over the extended cylinder shaft and the cylinder journal, and wherein the cylinder journal retains axial alignments of the tapered cylinder poppet spring along the central axis.

14. The method of claim 10, wherein the suction annulus comprises a plurality of protruding fingers that extend radially toward the central axis.

15. The method of claim 14, wherein the central axis is perpendicular to the suction annulus.

\* \* \* \* \*